United States Patent [19]

Frohn

[11] 4,255,138

[45] Mar. 10, 1981

[54] APPARATUS FOR USE IN MAXILLARY ORTHOPAEDICS

[76] Inventor: Hermann-Josef Frohn, Am Römerlager 4, D-5300 Bonn 1, Fed. Rep. of Germany

[21] Appl. No.: 71,500

[22] Filed: Aug. 31, 1979

[51] Int. Cl.³ .............................................. A61C 7/00
[52] U.S. Cl. ......................................................... 433/6
[58] Field of Search ..................................... 433/5, 6, 7

[56] References Cited

U.S. PATENT DOCUMENTS 3,885,310  5/1975  Northcott ................................ 433/5

Primary Examiner—Robert Peshock

Attorney, Agent, or Firm—Spensley, Horn, Jubas & Lubitz

[57] ABSTRACT

Apparatus for use in maxillary orthopaedics comprises a time-measuring device 18 fitted in a cavity in a moulding means 13 which is made of plastics material and is carried in the mouth. The time-measuring device 18 consists of an electronic counter which is connected to an impulse generator. The impulse generator is actuated by a switch 17 which is arranged to be in a different state according to whether the device is worn or not. The time-measuring device is connected, via leads 20' and switch 17, to a battery 16 also fitted in a cavity in the moulding means 13.

21 Claims, 9 Drawing Figures

APPARATUS FOR USE IN MAXILLARY ORTHOPAEDICS

The invention relates to an apparatus for use in maxillary orthopaedics, said apparatus comprising a moulding means which can be pressed against the teeth and carries a time-measuring device which is caused to function by means of a switch which is actuated when the apparatus is held in the mouth.

Apparatus of this kind used in maxillary orthopaedics are employed for the adjustment of teeth particularly in the case of growing children. The success achieved in maxillary orthopaedic treatment in which removable apparatus is used depends to a large extent upon whether the apparatus is actually held in the mouth over fairly lengthy periods. In many cases the dentist is held responsible for lack of success or unsatisfactory therapeutical results in orthopaedic treatment of the maxillae, whereas the unsatisfactory result stems from the fact that the apparatus was not retained for a sufficient length of time.

It is known to provide a time-measuring device, consisting of a Coulombmeter, on the moulding means in apparatus used in maxillary orthopaedics (German OS 26 14 591). The Coulombmeter, together with the moulding means is secured in the mouth of the patient. The Coulombmeter consists of a glass container with mercury and an electrolyte in it. When current is caused to flow through the Coulombmeter, the quantity of electrolyte passes slowly through the mercury. The product of current-strength and time can be read off at the point of separation of the two mercury columns. The Coulombmeter is switched on by way of a series arrangement consisting of a humidity switch and a temperature switch. In this method of measurement, the time for which the apparatus is held in the mouth is measured by determining the product of current-strength and time. Fitting of the Coulombmeter in the oral cavity is a dangerous matter since, in the event of damage to the glass container, not only are splinters of glass deposited in the mouth, but mercury and electrolyte as well.

In a known extra-oral apparatus (U.S. Pat. No. 3,885,310), a strap is fitted around the head of the patient, which strap is connected to the orthopaedic apparatus by way of the oral orifice. Provided on the strap is a time-measuring device which is caused to operate when the tension of the strap reaches a certain value. The time-measuring device consists of an impulse generator and a counter. The state of fill of this counter is intended to provide an indication of the period during which the apparatus is held in the mouth and is taken into account when judging the success of the treatment. In apparatus of this kind, stretching of the head-strap can easily cause the switch to close without the apparatus being worn by the patient.

The present invention seeks to provide apparatus of the originally stated kind for use in maxillary orthopaedics that constitutes no danger to the patient, enables the time that is to be determined to be measured relatively accurately, and to a large extent can be manipulated with safety.

According to the invention, there is provided apparatus for use in maxillary orthopaedics, said apparatus comprising a moulding means which can be pressed against the teeth, which moulding means carries a time-measuring device which is caused to function by means of a switch actuated when the apparatus is held in the mouth, said time-measuring device comprising an electric circuit including an electronic counter connected to an impulse generator, and a battery which is encased and accommodated in at least one cavity formed in the moulding means.

By fitting the electronic time-measuring device in a cavity in the moulding means, the time-measuring device is accommodated in a safe manner and is protected against mechanical damage. Even in the event of damage, the patient would be exposed to no danger since the time-measuring device contains no poisonous or otherwise dangerous substances. The time-measuring device enables the time that is of interest to be determined very accurately so that the dentist carrying out the treatment is able to determine its success in a very precise manner. Miniaturized electronic components as well as batteries are obtainable in sufficiently small dimensions, so that the dimensions of the moulding means are not greatly increased by the presence of the time-measuring device. If the various parts of the time-measuring device are fitted in different cavities formed in the moulding means, they can be interconnected by electric conductors extending within the moulding means. The electric conductors can be incorporated in the moulding means by a moulding operation, so that they are likewise protected against damage and moisture.

The impulse generator used can take the form of a quartz crystal-controlled oscillator which produces impulses at a predetermined constant frequency. These impulses are passed to the counter or impulse store which displays the number of impulses. This display can either take the form of a numerical display on the time-measuring device itself, or it may comprise a recording instrument that is available to the dentist and to which is connected the time-measuring device for the purpose of displaying the state of fill of the counter.

Since, during the treatment period, the apparatus for orthopaedic treatment of the maxillae has to be held in the mouth practically the whole time, less trouble is involved in determining and measuring the time during which the apparatus is not held in the mouth, since, in intensive treatment, this time is shorter than the period during which it is in the mouth. Whether the apparatus is or is not held in the mouth is determined with the aid of the switch which should be so designed or arranged that, during handling, it can not be actuated by a mischievous patient when the apparatus is removed from the mouth.

The apparatus in accordance with the invention is suitable not only for controlling the total time during which it is in the mouth, but can be so designed that the electrical circuit comprises a plurality of impulse stores which store details of the length of a closed phase and of an open phase of the switch and release these data when required. Thus, as in a log recorder, the in-the-mouth and the out-of-the-mouth times can be determined and recalled at a given time. This differentiated time measurement is particularly suitable for scientific investigations aimed at determining the effect of in-the-mouth times on adjustment of the teeth.

In order to prevent the switch from being deliberately actuated by the patient so that the dentist is deceived into thinking that the apparatus has been worn for a longer period, the switch is expediently accommodated in a covered position. A further possibility resides in providing a plurality of switches which are all actuated when the apparatus is worn in the mouth and are operated in series. This makes it more difficult to effect manipulations for falsifying the results of measurements.

The battery and the electric circuit can be accommodated in a moisture-proof manner in separate containers or in a common container and can be interconnected by electric conductors. The container in which the battery is housed must of course be capable of being opened in order to change the battery.

Switches that can be used are mechanical micro-switches, approximation switches, pressure sensors or contact-less switches. Particularly suitable are piezo-electric sensors or pressure-sensitive semi-conductors. The term "switch" is here intended to cover all devices that perform a switching operation when a particular physical condition occurs (pressure, moisture, etc.).

In order that the invention may be better understood, an embodiment thereof will now be described by way of example only and with reference to the accompanying drawings in which:-

Figure 1:
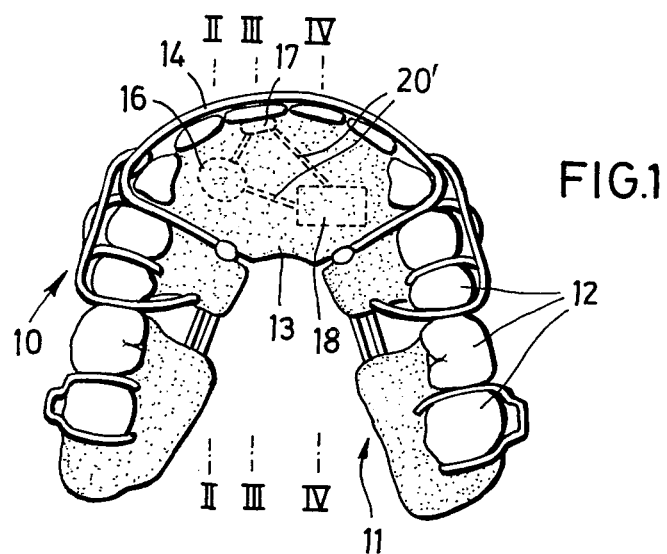
FIG. 1 shows an upper maxilla, and illustrates the arrangement of the elements of the time-measuring device in the apparatus of the invention.
Figure 8:
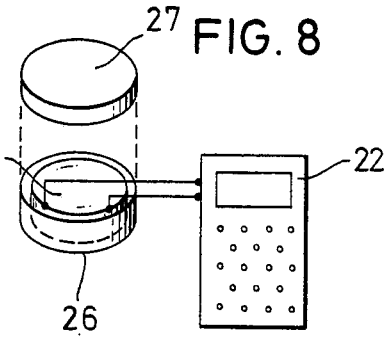
Figure 9:
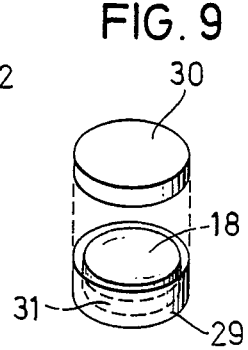

FIG. 8 is a perspective view of a capsule for the time-measuring device, connected to an external reading instrument; and FIG. 9 is a diagrammatic view of a capsule for a time-measuring device having its own numerical display means. FIG. 1 illustrates an upper maxilla 10, the shape of which is to be altered by means of an orthopaedic apparatus 11. The teeth are designated by the numeral 12. The orthopaedic apparatus consists of at least one plastics moulding means 13, to which are secured wire braces 14 which entirely or partially surround the teeth. Use may also be made of a plurality of plastics moulding means which are interconnected by wire braces. The shape of the apparatus will depend upon the shape of the particular maxilla and the defects to be corrected.

Figure 2:
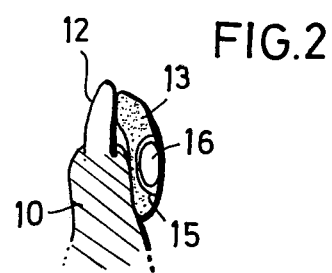
FIGS. 2, 3 and 4 illustrate cross-sections of the maxilla along the lines II, III and IV respectively of FIG. 1.

FIG. 2 shows a plastics moulding means 13 which presses against a tooth 12 and contains, in a first cavity 15, a miniature battery 16. The cavity 15 is closed by a plate so that it is shut off from the exterior.

Figure 3:
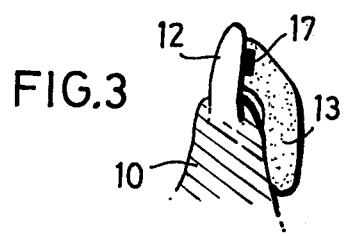
Figure 4:
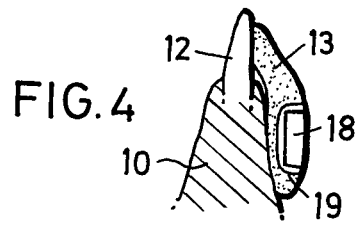

In FIG. 3 can be seen the switch or pressure sensor 17 which presses against the tooth 12 and is actuated thereby. The pressure sensor 17 is positioned at the outer end of the moulding means 13, which end presses against the tooth.

In a further cavity 19 in the moulding means 13 is arranged a time-measuring device 18. This cavity is also closed off from the exterior. The battery 16, the pressure sensor 17 and the time-measuring means 18 are interconnected by electric conductors 20'.

Figure 5:
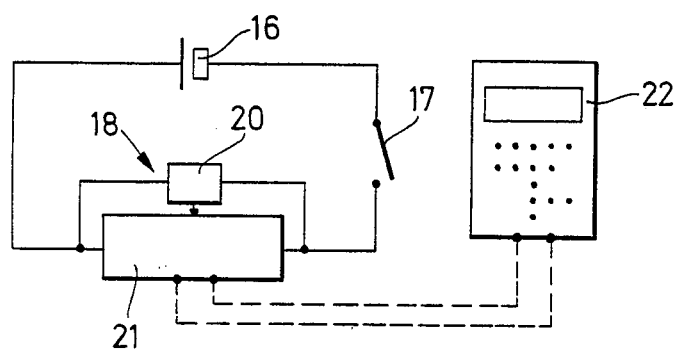
FIG. 5 is a block diagram showing the interconnections relating to the time-measuring device.

The electric circuit for the time-measuring device is illustrated in FIG. 5 as a block diagram. The time-measuring device 18 and the switch or pressure sensor 17 are connected in series across the battery 16. When the switch 17 is closed, the time-measuring device 18 is set in operation. The time-measuring device consists of an impulse-generator 20 which, when connected to the current supply, produces impulses at a particular frequency. These impulses are passed to a counter 21 which counts the impulses and also stores the result of the particular count when the switch 17 is opened again. The state of count of the counter 21 is therefore a measure of the time for which the switch 17 has been closed.

The time-measuring device 18 is advantageously constructed by making use of integrated circuitry.

The time-measuring device 18 can be removed from the cavity 19 and connected to a reading instrument 22 in order to indicate the state of count of the counter 21. It is also possible for the time-measuring device to remain in the capsule and to be connected to a reading instrument, and this, in certain circumstances, is easier for the dentist.

Figure 6:
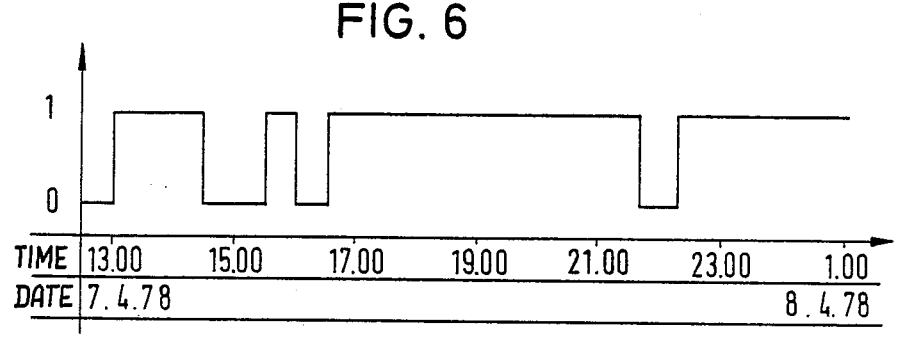
FIG. 6 is a time plot showing one example of a possible way of recording the length of successive wearing and non-wearing periods.

If the time-measuring device comprises a plurality of counters that can be actuated in succession and in turn indicate the wearing times and the non-wearing times, they can perform a recording function as shown in FIG. 6. When a time-measuring device of this kind is read, the entire wearing cycle between two treatment dates can be reproduced by reading the store with the aid of, for example, a connected recording instrument or a high-speed printing means. In FIG. 6, the wearing times are designated by "1" and the non-wearing times by "0". The time-measuring device can incorporate a clock, the time indications of which are passed into a store each time the switch 17 is actuated. In this way the times during which the apparatus is removed or inserted are stored. These data can then be passed to the reading apparatus or to some other apparatus for carrying out further processing.

Figure 7:
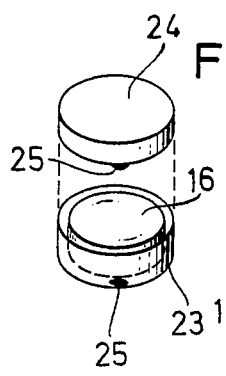
FIG. 7 is a perspective view of a capsule for the battery.

FIG. 7 shows a capsule 23 which is closed in a fluid-tight manner by a cap 24 and which encloses a battery 16. At the bottom of the capsule and the cap are located contact poles 25 for establishing contact with the poles of the battery 16. The contact poles 25 are connected by conductors (not shown) to other electrical components. When the cap 24 of the capsule is screwed on, these poles press against the battery poles.

As shown in FIG. 8, a similar capsule 26 with a cap 27 is used for accommodating the time-measuring device 18. This capsule is also sealed off in a moisture-tight manner. The time-measuring device 18 has terminals to which the reading apparatus 22 can be connected in order to display the state of fill of the counter. Thus, when the counter is read in the dental surgery, the period during which the apparatus has been worn can be determined.

FIG. 9 illustrates a capsule 29 which is sealed by a cap 30 and contains a time-measuring device 18 having a miniaturized number-display means 31. By means of this, the period during which the apparatus has been worn can be read off directly, if necessary by the user himself, without connection to an external reading instrument being required.

In day-to-day practice, two items of information can be of considerable importance to the dentist:
1. the total wearing time in hours, which time can be indicated on call, and
2. the entire non-wearing time in hours, which can likewise be indicated on call.

In this way, the dentist is able to determine in an objective manner the success obtained by wearing the apparatus.

I claim:

1. For use in maxillary orthopaedics wherein a moulding means which can be pressed against the teeth is worn in the mouth to adjust the position of the teeth, an apparatus for measuring the wearing time of said moulding means, comprising:

a time-measuring device carried by said moulding means and actuated by a switch, also carried by said moulding means, when the moulding means is held in the mouth, said time-measuring device comprising an electric circuit including an electronic counter connected to an impulse generator, and a battery, said time-measuring device and said battery being encased and accommodated in at least one cavity formed in the moulding means.

2. Apparatus according to claim 1 wherein the switch is so carried by said moulding means that it is closed during the time that the moulding means is not carried in the mouth, and is opened during the time that the moulding means is carried in the mouth.

3. Apparatus according to claim 1 or 2 wherein the time-measuring device includes a numerical display means connected to said electronic counter so as to display a time readout corresponding to the contents of said counter.

4. Apparatus according to claim 1 wherein the battery and the electric circuit are accommodated in a moisture-proof manner in separate containers and are interconnected by electric conductors.

5. Apparatus according to claim 1 wherein the switch is a pressure sensor which senses the pressure exerted between said moulding means and part of the mouth upon which said moulding means acts when said moulding means is placed in the mouth.

6. Apparatus according to claim 1 wherein the electric circuit further includes a plurality of storage devices which in turn store information relating to the successive durations that said switch was open and closed, and that release the information when appropriately accessed.

7. Apparatus according to claim 1 wherein said switch comprises a plurality of switches which are all actuated when the moulding means is held in the mouth, and which must be operated in series to cause said time-measuring device to function.

8. Apparatus according to claim 1 wherein said moulding means is substantially externally dimensionally and configurationally unaltered by the presence of said encased battery and time-measuring device.

9. Apparatus according to claim 1 wherein the external dimensions of said moulding means are not substantially changed from what said dimensions would have been if said moulding means had been designed not to accommodate said time-measuring device, said battery and said switch.

10. Apparatus according to claim 1 further comprising a separate read-out means, external to the moulding means, for reading and displaying the measured time corresponding to the contents of said electronic counter.

11. A device for measuring the time that a retainer or like removable orthodontic appliance is worn in the mouth, comprising:

a time-measuring circuit encased within said appliance, and switch means, mounted in said appliance for activation when said appliance is placed in the mouth, for enabling said time-measuring circuit when said switch means is activated, said time-measuring circuit thereby measuring how long said appliance has been worn.

12. A device according to claim 11 wherein said time-measuring circuit comprises:

a pulse generator producing pulses at certain time intervals, and a counter connected to count pulses from said generator when said time-measuring circuit is enabled.

13. A device according to claim 11 wherein said switch means is encased within said appliance.

14. A device for measuring the time that a retainer or like removable orthodontic appliance is worn in the mouth, comprising:

switch means, mounted in said appliance for activation when said appliance is placed in the mouth and for deactivation when said appliance is removed from the mouth;

a time-measuring circuit encased within said appliance having a first set of time-measuring devices connected to be enabled sequentially upon sequential activation of said switch means each time said appliance is placed in the mouth, so that each of said first set of time-measuring devices will measure how long said appliance has been worn in the mouth during corresponding sequential periods of wear, and a second set of time-measuring devices connected to be enabled sequentially upon sequential deactivation of said switch means each time said appliance is removed from the mouth, so that each of said second set of time-measuring devices will measure how long said appliance has not been worn during corresponding periods when the appliance is removed.

15. A device according to claim 14 together with:

readout means, external to said appliance but connectable to said time-measuring circuit, for reading out and displaying the sequential times that said appliance was worn and not worn, as measured by said first and second sets of time-measuring devices.

16. A device according to claim 14 or 15 wherein said time-measuring circuit includes a pulse generator, and wherein each of said time-measuring devices comprises a separate counter connected to count pulses from said generator when the respective time-measuring device is enabled.

17. A device according to claim 15 wherein said readout means includes:

display means for presenting from said measured times a chronological display indicating which hours of the day the appliance was worn and which hours the appliance was removed from the mouth.

18. A device according to claim 11 wherein said switch means comprises a pressure sensor mounted within said activated appliance so as to be activated by pressure exerted between the teeth and said appliance when said appliance is placed in the mouth.

19. A device according to claim 11 or 18 wherein the dimensions of said appliance are not substantially changed from what they would have been if said appliance had been designed without accommodation for said time-measuring circuit and said switch.

20. A device for measuring the time that a retainer or like removable orthodontic appliance is worn in the mouth comprising:

a time-measuring circuit encased within said appliance having
- a first means for measuring and storing the times during which said appliance has been worn in the mouth, and
- a second means for measuring and storing the times during which said appliance has not been worn;

switch means, mounted in said appliance for activation when said appliance is placed in the mouth and for deactivation when said appliance is removed from the mouth for enabling said time-measuring circuit;

readout means, external to said appliance but connectable to said first and second means, for reading out and displaying in chronological order the measured and stored times during which said appliance was worn and not worn.

21. For use in maxillary orthopaedics wherein a moulding means which can be pressed against the teeth is worn in the mouth to adjust the position of the teeth, an apparatus for measuring the wearing time of said moulding means, comprising:
- a time-measuring device carried by said moulding means and actuated by a switch when the moulding means is held in the mouth, said time-measuring device comprising an electric circuit including an electronic counter connected to an impulse generator, and
- a battery, said time-measuring device, said battery and said switch being encased and accommodated in at least one cavity formed in the moulding means and said moulding means being in substantial part externally unaltered in shape by the presence of said encased and accommodated time-measuring device, battery and switch.

* * * * *